(12) United States Patent
Solie (10) Patent No.: US 12,009,110 B1
(45) Date of Patent: *Jun. 11, 2024

(54) METHOD FOR USING A CLINICIAN STATION TO PROVIDE MEDICAL SERVICES REMOTELY

(71) Applicant: MD Health RX Solutions, LLC, Tampa, FL (US)

(72) Inventor: Leonard Solie, Clearwater, FL (US)

(73) Assignee: MD Health RX Solutions, LLC, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/723,264

(22) Filed: Dec. 20, 2019

Related U.S. Application Data (63) Continuation of application No. 16/692,908, filed on Nov. 22, 2019, which is a continuation-in-part of application No. 16/275,741, filed on Feb. 14, 2019, which is a continuation-in-part of application No. 13/777,864, filed on Feb. 26, 2013, now abandoned.

(Continued)

(51) Int. Cl.
*G16H 80/00* (2018.01)
*A61B 5/00* (2006.01)
*A61B 5/117* (2016.01)
*G16H 40/67* (2018.01)
(Continued)

(52) U.S. Cl.
CPC ........... *G16H 80/00* (2018.01); *A61B 5/0022* (2013.01); *A61B 5/117* (2013.01); *A61B 5/742* (2013.01); *A61B 5/7465* (2013.01); *G16H 40/67* (2018.01); *G16H 50/20* (2018.01); *H04L 63/0884* (2013.01)

(58) Field of Classification Search
None
See application file for complete search history.

(56) References Cited

U.S. PATENT DOCUMENTS 6,046,761 A   4/2000   Echerer
6,205,716 B1  3/2001   Peltz
(Continued)

FOREIGN PATENT DOCUMENTS

WO         02096339 A1    12/2002
WO     WO-2014002091 A2 *  1/2014  ......... H04N 1/19594

OTHER PUBLICATIONS

Onmed, OnMed Kiosk, May 9, 2019 <https://web.archive.org/web/20190509133902/https://onmed.com/> (Year: 2019).*

(Continued)

*Primary Examiner* — Gregory Lultschik
(74) *Attorney, Agent, or Firm* — Padda Law Group (57) ABSTRACT

A clinician station supporting private and secure telemedicine session between an operator and a patient on a remote patient station terminal. The clinician stations comprising a base, an interactive device stand, and a display terminal. The interactive device stand includes an electronic device, a device casing, and an adjustable arm. The display terminal includes a display device, a display casing, and an adjustable arm. The electronic device and the electronic display device are electronically communicable over a network with a cloud based system that is configured to host a medical session between a patient in the patient station terminal and the operator using the clinician station.

17 Claims, 10 Drawing Sheets

Related U.S. Application Data (60) Provisional application No. 61/606,095, filed on Mar. 2, 2012.

(51) Int. Cl.
*G16H 50/20* (2018.01)
*H04L 9/40* (2022.01)

(56) References Cited

U.S. PATENT DOCUMENTS

| | | | |
|---|---|---|---|
| 6,428,124 | B1 | 8/2002 | Bluth et al. |
| D501,557 | S | 2/2005 | Collins et al. |
| 7,445,600 | B1 | 11/2008 | Carr et al. |
| 7,912,733 | B2 | 3/2011 | Clements et al. |
| 9,261,262 | B1* | 2/2016 | Baloga ............ G06Q 10/06311 |
| 10,233,659 | B1* | 3/2019 | Holdredge ............ A47B 23/043 |
| 2002/0104271 | A1 | 8/2002 | Gallant |
| 2004/0044560 | A1 | 3/2004 | Giglio et al. |
| 2004/0090424 | A1 | 5/2004 | Hurley |
| 2004/0145676 | A1* | 7/2004 | Lin .................... H04N 5/2251 348/E5.025 |
| 2005/0075907 | A1 | 4/2005 | Rao |
| 2005/0239037 | A1 | 10/2005 | Lertsithichai |
| 2006/0106646 | A1 | 5/2006 | Squilla et al. |
| 2006/0143997 | A1 | 7/2006 | Libenson |
| 2006/0173267 | A1 | 8/2006 | Chiang et al. |
| 2006/0271400 | A1* | 11/2006 | Clements ............ G16H 80/00 705/2 |
| 2006/0290885 | A1 | 12/2006 | Covannon et al. |
| 2007/0073113 | A1 | 3/2007 | Squilla et al. |
| 2009/0137047 | A1 | 5/2009 | Regan et al. |
| 2009/0160876 | A1 | 6/2009 | King et al. |
| 2009/0167838 | A1* | 7/2009 | Poisner ................ G16H 80/00 348/14.04 |
| 2009/0233769 | A1 | 9/2009 | Pryor |
| 2009/0240527 | A1 | 9/2009 | Bluth |
| 2009/0276242 | A1 | 11/2009 | Waisbren |
| 2010/0222649 | A1* | 9/2010 | Schoenberg ........ G16H 40/67 600/301 |
| 2011/0014955 | A1 | 1/2011 | Kim |
| 2011/0122995 | A1* | 5/2011 | Ferro, Jr. ................ G06F 19/00 378/62 |
| 2011/0130635 | A1 | 6/2011 | Ross |
| 2011/0191123 | A1 | 8/2011 | Buzynski |
| 2012/0179479 | A1* | 7/2012 | Waterson .............. G16H 80/00 705/2 |
| 2012/0275167 | A1* | 11/2012 | Scruggs .................... F21V 7/06 362/296.08 |
| 2013/0246084 | A1* | 9/2013 | Parmanto ............. G16H 40/67 705/2 |
| 2013/0314852 | A1* | 11/2013 | Kincaid ............ F16M 11/046 361/679.01 |
| 2014/0081656 | A1* | 3/2014 | Alamri .................. G16H 80/00 705/3 |
| 2014/0095196 | A1 | 4/2014 | Waterson |
| 2014/0139616 | A1 | 5/2014 | Pinter |
| 2014/0330579 | A1* | 11/2014 | Cashman ............. E04H 1/1222 705/2 |
| 2015/0042822 | A1 | 2/2015 | Le |
| 2015/0248536 | A1* | 9/2015 | Tawil .................... G16H 30/20 705/3 |
| 2016/0105641 | A1* | 4/2016 | Periyannan ............. H04L 12/18 348/14.08 |
| 2017/0032092 | A1* | 2/2017 | Mink ................ G06Q 10/06311 |
| 2018/0110475 | A1* | 4/2018 | Shaya .............. G06Q 10/06311 |
| 2020/0027568 | A1* | 1/2020 | Foshee, Jr. .............. G06F 13/20 |

OTHER PUBLICATIONS

W. -P. Lu, H. Leung and E. Estrada, "Transforming telemedicine for rural and urban communities Telemedicine 2.0—any doctor, any place, any time," The 12th IEEE International Conference on e-Health Networking, Applications and Services, Lyon, France, 2010, pp. 379-385 (Year: 2010).*

Screen shot of Internet web site http://bigthink.com—Teaches virtual doctor in a kiosk Link: http://bigthink.com/ideas/40455?page=all.

Screen shot of Internet web site www.emrandehr.com—Teaches virtual doctor in a kiosk Link: http://www.emrandehr.com/2011/10/03/virtual-doc-kiosks-a-giant-leap-for-telehealth/.

Screen shot of Internet web site www.fastcompany.com http://www.fastcompany.com/magazine/155/the-virtual-doctor-will-see-you-now.html.

Screen shot of Internet web site www.medlegalsource.com—teaches a combined medical/legal consulting website Link: http://www.medlegalsource.com/terms-of-use.

* cited by examiner

METHOD FOR USING A CLINICIAN STATION TO PROVIDE MEDICAL SERVICES REMOTELY

CROSS-REFERENCE TO RELATED APPLICATIONS

This U.S. nonprovisional patent application is a continuation application of US. nonprovisional patent application Ser. No. 16/692,908 filed on Nov. 22, 2019, which claims the benefit of U.S. nonprovisional patent application Ser. No. 16/275,741, filed on Feb. 14, 2019, which claims the benefit of U.S. nonprovisional patent application Ser. No. 13/777,864, filed on Feb. 26, 2013, which, in-turn, claims the benefit of U.S. provisional patent application Ser. No. 61/606,095, filed on Mar. 2, 2012, all-of-which are incorporated-by-reference herein in their entirety.

FIELD OF THE INVENTION

The present invention relates generally to a clinician station, and more particularly, to a clinician station that allows a clinician to communicate with a patient in a patient station during a remote medical session.

BACKGROUND OF THE INVENTION

Medical care is a need for every individual and every family. Many individuals have one or more physicians or other medical professionals that they see for wellness visits and for treatment of various illnesses and injuries. As the population continues to grow and healthcare continues to evolve, however, the need for doctors and health care providers continues to grow. Because of this growth, medical facilities such as hospitals and doctors' offices are operating at maximum physical capacity. Since the population continues to grow and the need for doctors and health care providers is not expected to abate in the near or immediate future, there is a need for an alternative more efficient manner to see patients rather than physically seeing them on-site.

Medical facilities in general have been attempting to improve efficiency through utilizing technology. In particular, some aspects of patient care have been computerized through the use of electronic terminals interactively accessible to the patients. Currently, processes such as checking in and prescription refill requests may be handled entirely by digital mediums. These digital mediums may be in the form of specialized hardware and software for collecting, organizing, and updating information associated with patients.

Hospitals and medical clinics recently began utilizing interactive devices that allow patients to perform routine activities. The ability for patients to perform operations such as update personal information linked to their health profile, pay medical fees, and other various routine activities via these interactive devices has generated a significant increase in efficiency for medical facilities. However, patients are still required to be physically on-site in order for medical professionals to perform routine medical activities that are necessary to treat a patient such as measuring vital signs.

There have also been limitations regarding doctor and medical professional availability in the case when an individual requires immediate attention. For example, if an individual were to decide to visit a doctor or medical professional's office for a non-emergency the day of, then that individual would be classified as a "walk-in" if he or she did not have an appointment and would be subjected to a wait time associated with the current workload of the medical facility. The individual's only alternative would be to go the emergency room of a hospital for a non-emergency matter.

Recently, there have been developments in implementations of various systems and methods relating to telehealth and telemedicine. These systems and methods, however, require a substantial amount of improvement in order for them to be nearly as efficient as the conventional practice of medicine.

Thus, there is a need for a medical services system that allows doctors and other medical professionals to examine, diagnose, and treat patients without requiring the patients to be physically present with the medical professional.

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

SUMMARY OF THE INVENTION

The present invention is directed to a clinician station that includes a plurality of equipment that allows a user, operator, or clinician to oversee and or administer basic physical examinations performed by a patient inside of a medical kiosk over a network. The medical services kiosk the patient utilizes for the remote exam generally comprises a patient station that satisfies the need for providing facilities for remote interaction with the health care professionals interacting with the clinician station overseeing the medical exam in real time.

Introducing a first embodiment of a clinician station, comprising:
a base;
an interactive device stand coupled to the base; and
a display terminal coupled to the base facing the interactive device,
wherein the clinician station is electronically communicable over a network with a cloud based system configurable to host a medical session between a patient in a patient station and an operator using the clinician station.

In another aspect, the operator may be any one of a nurse, a doctor, a pharmacist, a nurse practitioner, a nursing assistant and a clinician.

In another aspect, the base may have a footwell about a front end of the base for receiving the operator's feet therein.

In another aspect, an LED light source may be attachable to a bottom end of the base.

In another aspect, the LED light source is programmable to emit a specific color-coded light according to said operator's title.

In yet another aspect, the interactive device stand comprises,
an electronic device electronically communicable with the cloud based system hosting the medical session;
a device casing having a depression for retaining the electronic device therein; and
an adjustable arm extending upwardly from the base and coupled to a bottom portion of the device casing.

In another aspect, the adjustable arm may be a telescopic arm that includes a plurality of members insertable and slidable within one another allowing said operator to selectively adjust the interactive device stand to a desirable height.

In another aspect, the electronic device may be an electronic smart tablet.

In another aspect, the display terminal comprises,
an electronic display device electronically communicable with the cloud based system hosting the medical session;
a display casing having an opening for receiving the electronic display device therein; and
an adjustable arm extending upwardly from the base and coupled to a bottom portion of the display casing.

In yet another aspect, the adjustable arm may be a telescopic arm that includes a plurality of members insertable and slidable within one another allowing said operator to selectively adjust the display terminal to a desirable height.

In yet another aspect, the display casing generally includes a top, a front, a back, opposite right and left sides, and an interior spacing.

In another aspect, the back of the display casing may include a ventilation grill positioned above an access panel, the access panel provides the operator access to the interior space of the display casing.

In a second embodiment, a clinician station, comprising:
a base having a top end, a bottom end, a front end, a back end, and a footwell about the front end of said base for receiving an operator's feet therein, the base further including an LED light source attachable to the bottom end of the base;
an interactive device stand, comprising
    an electronic device,
    a device casing having a depression for retaining the electronic device therein, and
    an adjustable arm extending upwardly from the base and coupled to a bottom portion of the device casing; and
a display terminal, comprising
    an electronic display device;
    a display casing having an opening for receiving the electronic display device therein; and
    an adjustable arm extending upwardly from the base and coupled to a bottom portion of the display casing,
    wherein the electronic device and the electronic display device are electronically communicable over a network with a cloud based system configurable to host a medical session between a patient in a patient station and an operator using said clinician station.

In a third embodiment, a clinician station, comprising:
a base having a top end, a bottom end, a front end, a back end, and a footwell about the front end of the base for receiving an operator's feet therein, the base further including an LED light source attachable to the bottom end and programmable to emit a specific color-coded light according to the operator's title;
an interactive device stand, comprising
    a smart tablet,
    a device casing having a depression for retaining the smart tablet therein, and
    a telescopic arm that includes a plurality of members insertable and slidable within one another allowing the operator to selectively adjust the interactive device stand to a desirable height; and
a display terminal, comprising
    an electronic display device;
    a display casing that includes a top, a front, a back, opposite right and left sides, an interior spacing, and an opening for receiving and retaining the electronic display device therein, the display casing further includes a ventilation grill positioned above an access panel giving the operator access to the interior space of the display casing; and
    telescopic arm that includes a plurality of members insertable and slidable within one another allowing the operator to selectively adjust the display terminal to a desirable height,
    wherein the smart tablet and the electronic display device are electronically communicable over a network with a cloud based system configurable to host a medical session between a patient in a patient station and an operator using the clinician station, during the medical session the operator having functional control over a plurality of systems provided inside of the patient station.

In an another embodiment, the present invention may include the method of providing remote real time patient ailment diagnoses and treatment, said method including the steps of:
providing a clinician station communicable over a network;
providing a patient station communicable over said network;
providing a cloud based system communicable over said network;
requiring an identification process before being able to use said clinician station;
requiring a patient to enter said patient station and request a medical session;
activating a search query by said cloud based system for an available operator to match with said patient;
linking said clinician station with said available operator with said patient in said patient station to establish said medical session, said medical session hosted by said cloud based system over said network;
enabling bi-lateral communication between said available operator in said clinician station and said patient in said patient station; and
disconnecting said clinician station from said patient station.

As described herein, medical professional may include but is not limited to any doctor, pharmacist, nurse practitioner, nurse, nursing assistant, or any other individual who examines and treats or assists in the examination and treatment of patients for medical purposes.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
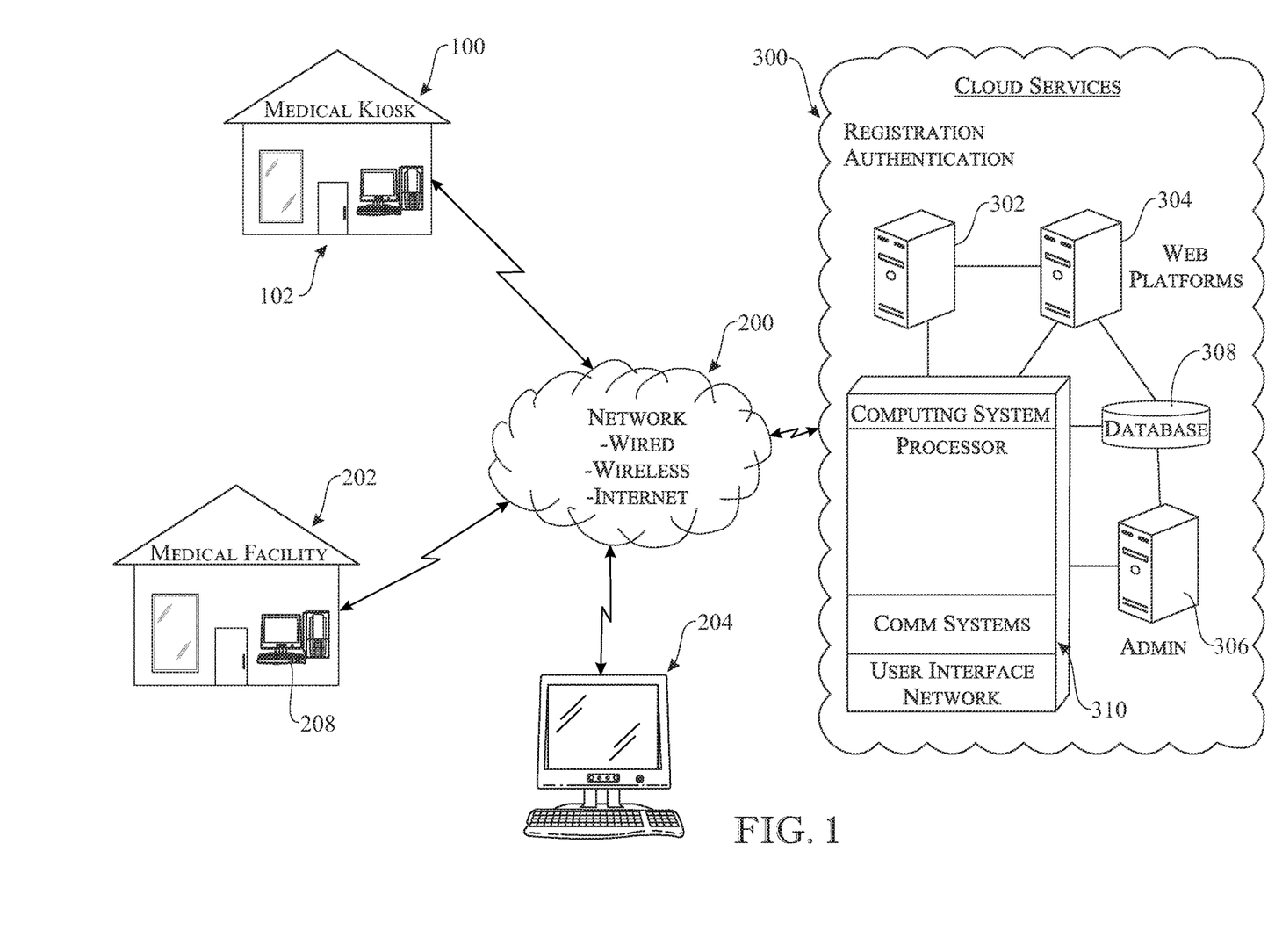
FIG. 1 presents a schematic view of a facility having at least one clinician station therein communicatively coupled to a medical kiosk located remotely thereof, both the medical service kiosk and facility communicatively coupled to a cloud based server via a network.

Initially referring to FIG. 1 there is shown a schematic view of a remote real time medical assistance system, showing a medical service kiosk 100, and a medical facility 202 in bidirectional communication and hosted on a cloud based services system 300 over an accessible communication network 200, in accordance with an embodiment of the present invention. It is appreciated that any number of medical service kiosks 100 and medical facilities 202, which can include one or more terminals, computers or servers, can access and use the cloud services system 300. As illustrated in FIG. 1, the medical service kiosk 100 and medical facility 202 communicates with the cloud services system 300 via a wired, wireless, or internet connection network 200. The medical service kiosk 100 gives access to at least one patient to a secure medical session with a clinician, a physician, or healthcare professional that is located at the remote medical facility 202 operating a clinician station, or on a remote electronic device 204 at a remote location, such as their office, home, or an alternative remote location over the network terminal 200. Patient access to the medical session with a clinician or physician at a medical facility 202 hosted by the cloud services system 300, is accomplished by use of an electronic device including any of, but not limited to, a tablet, laptop or notebook computer, or a desktop computer. It is appreciated that each medical session may be recorded and stored in memory or a database 308 provided by the cloud services system 300 for later viewing. In application, each electronic device includes the necessary electronic components required to communicate with the medical kiosk 100, medical facility 202, and cloud services system 300. As such, each patient and clinician electronic device may include audio and video circuitry, a keyboard or touchpad, memory or access to memory, one or more processors, I/O network interface, application program interface, read/write memory (RAM), read-only memory (ROM), and a visual screen or display for navigating through a medical session hosted on the cloud services system 300.

Each electronic device utilized to connect to the cloud services system 300, hosting the medical session, electrically communicates via a wired (landline), wireless, or internet network including VOIP (voice over internet protocol) network. The communication network 200 may include wireless communication including but not limited to: WLAN (wireless local area network, Wi-Fi (IEEE 802.11), WPANS (wireless personal area networks, such as Bluetooth (IEEE 802.15), Infrared, ZigBee), WMAN (wireless metropolitan area network, such as WiMax (IEEE 802.16)), WWAN (wireless wide area networks, internet), and GAN (global area network), a mobile wireless communication system, such as 3G, 4G, or 5G, an internet-protocol based communication system. The communication network 200 may include a wired communication including but not limited to, fiber optic systems, a telephone network such as a PSTN (public standard telephone network). The communication network 200 may further include a radio frequency network (RF), a cable network, a satellite network, and an internet or intranet network, where each network is adapted for transmitting, and receiving data, information, audio, video, texts, messages, emails, and files between the medical kiosk electronic devices and the medical facility 202, and cloud services system 300. It will be noted that network, interface, communication and information exchange equipment, components or peripherals may be employed, including, but not limited to, use of base stations, servers, routers, switches, repeaters, towers, antennas, Ethernet hubs, wired or wireless data pathways, modems, virtual private networks (VPN), modems, proxy servers, application program interfaces (APIs), networking adapters, or gateways. Encryption protocols may also be employed to secure the transmitted information, data, or messages. For example, a few exemplary forms of encryption include IPsec, or secure sockets layer (SSL), and symmetric or asymmetric encryption.

The cloud service system 300 comprises an internet based computing service system including in one embodiment, a user registration/authentication server 302, a web platform server 304, and an administrative server 306, all networked together by way of a central database 308, and computing system 310. The cloud service system 300 may include a public, private, or hybrid cloud configuration based on various cloud service models including any of an Iaas (Infrastructure as a Service), PaaS (Platform as a Service), or Saas (Software as a Service) model. The type of cloud configuration implemented is based on need for data security, control over the infrastructure, sensitivity of data and applications, and industry regulations or standards. In a preferred embodiment, the cloud computing services 300 comprises the Amazon Web Services (AWS) elastic compute cloud EC2 architecture that supports simple email service (SES), and simple notification service (SNS) to allow both email and short message service (SMS) communication between patients/medical care providers, and the AWS cloud computing services 300, via, electronic devices over network 200. The AWS cloud computing services 300 also supports simple storage service (a single web-services interface) to store and retrieve data from anywhere on the web.

With continued reference to FIG. 1, when a secure connection has been established with a health care professional or operator over the communication network 200, which will be described further herein below, the patient will be able to communicate with the operator (e.g., clinician, physician, pharmacist, nurse practitioner, nurse, nursing assistant, etc.) and provide the healthcare professional with medical information, either verbally, i.e., patient explanation of symptoms, or through the use of medical equipment provided inside of the patient station 102 that is connected to an electronic device therein to transmit readable data to the clinician station being operated by the operator overseeing the medical session. The operator will be able to guide and instruct the patient on how to use the equipment provided therein. The operator may use a user operable interface to some, if not all, of the equipment inside of the patient station of the medical service kiosk 100. The equipment inside of the patient station is communicable with the central processor of the electronic device inside of the patient station, and can transfer readable data to the cloud services system 300, and the network terminal accessible 208 or electronic device 204 being used by the physician overseeing the medical session. The physician may review the information (i.e., readable data) that is being transmitted in real-time on the user-operable interface, and may be able to render a medical opinion based on the readings. The operator or health care professional will also be able to provide medicine that can be dispensed by the medical kiosk medical storage space provided by the medical services kiosk 100, or, alternatively, remotely send a print command to a printer located at the medical kiosk to print a prescription or electronically send a prescription notification to a nearby pharmacy for pick-up. In one exemplary form, the medical services kiosk 100 and medical facility 202 may be connected to a back-up generator or to at least one uninterruptible power supply (UPS) battery that is powerful enough to energize the medical services kiosk and medical facility (including the clinician station), and particularly the equipment inside of each respective facility in the event of an unexpected power loss.

Referring now to FIGS. 1-5 and 8, the remote medical facility 202 may include a clinician station 210 in accordance with one exemplary embodiment of the present invention. The clinician station 210 may comprise a platform or base 212 having a top end 214 and a bottom end 222, opposite right and left sides 216, 218, and a rear end 224 and a front end 220. The front end 220 of the base 212 may include a footwell or opening 221 for receiving an operator's feet (e.g., a healthcare professional). The base 212 may include a multi-color light source 223, such as an LED light or the like disposed about the base's periphery and or footwell 221 to illuminate the bottom of the base 212 to a desirable color. The colors displayed by the light source 223, which are visible to the remote patient, may be used to indicate or inform the patient of the status, title, type, or designation of the operator engaged in the medical session. For instance, during the beginning of a medical session the patient interacting with the operator, which for the purposes of this example is a nurse, may see that the light being emitted by the light source 223 is a green-coded light. This notifies the patient that the person talking to him or her is a nurse. When the healthcare professional steps away and a different operator engages with the patient during the medical session the light being emitted by the light source 223 may change if the status or title of the professional is different (i.e., the operator is not a nurse). For example, in the case of a physician interacting with a patient following the exit of a nurse, the light emitted by the light source 223 may change from a green-coded light to a red-coded light to indicate to the patient that the operator's title has changed from a nurse to a physician. Additional symbol-coded, graphic-coded or any other suitable color combinations and means to indicate a distinction between two separate individuals with separate titles may be utilized without departing from the scope of the invention. The base 212 may further comprise an extendable electrical wire (not shown) that plugs into an electrical source (e.g., an electrical outlet) within the remote medical facility 202 in order to power the clinician station 210, and other electrical components connected thereto. Alternatively, the clinician station may include a separate power supply device (e.g., battery) that energizes the clinician station 210 in the event an electrical source or power is unavailable.

As illustrated in FIGS. 2-5, The clinician station 212 further comprises an interactive clinician device 226 that extends upwardly from the top end 214 and about the front end 220 of the station's base 212. The clinician device 226 comprises a telescopic arm 228 that is height adjustable. In one exemplary form, the telescopic arm 228 may include a first tube 230, a second tube 232, and a third tube 232 that are insertable and slidable within one another. The height of the clinician device may be adjusted to the height or preference of the operator either manually or automatically by mechanical means (e.g., pull and push force) and or electrical means (e.g., actuators). The telescopic arm 228 at a top end is attached to a holder or casing 234 that protects and holds an electronic device 236. In one exemplary form, the electronic device 236 used in the clinician device 226 is an electronic tablet. The electronic device 236 of the interactive clinician device 226 communicates with the communication network and cloud based system described heretofore with reference to FIG. 1. The clinician device 226 may also include a plurality of additional equipment 238 connected thereto. For example, the clinician device may also include an LED controller, a headset holder, a headset, and or a volume controller, all of which are accessible and usable by the operator accessing the clinician station 210.

With continued reference to FIGS. 1-5 and 8, at an opposite end of the interactive device 226 is a display terminal 238. The display terminal 238 extends upwardly from the top end 214 of the station's base 212 and at about the rear end 224 of the base 212. The display terminal 238 generally comprises a telescopic arm 248 that may include a first tube 250 and a second tube 252 (and perhaps even a third tube or more) that are insertable and slidable within one another. The overall height of the display terminal may be adjusted to an optimal height or to the preferential height of the operator by mechanical or electrical means. As previously stated herein above, mechanical means may include a mechanism that allows for a push and pull input force to drive the mechanism upwardly and downwardly, and electrical means may include a mechanism that is driven by electrical components, e.g., actuators or the like, to do the same. The telescopic arm 248 at a top end is attached to a bottom 246 of a shell or casing 240 that holds an electronic display 264. The casing 240 generally comprises a top 244, the bottom 246, a front 245, a back 256, and opposite right and left sides 242. The display terminal 238 may include lighting 258 disposed about the opposite right and left sides 242 of the casing 240. The lighting 258, in one exemplary form, may be provided in the form of elongated flat studio LED lighting bulbs.

Figure 3:
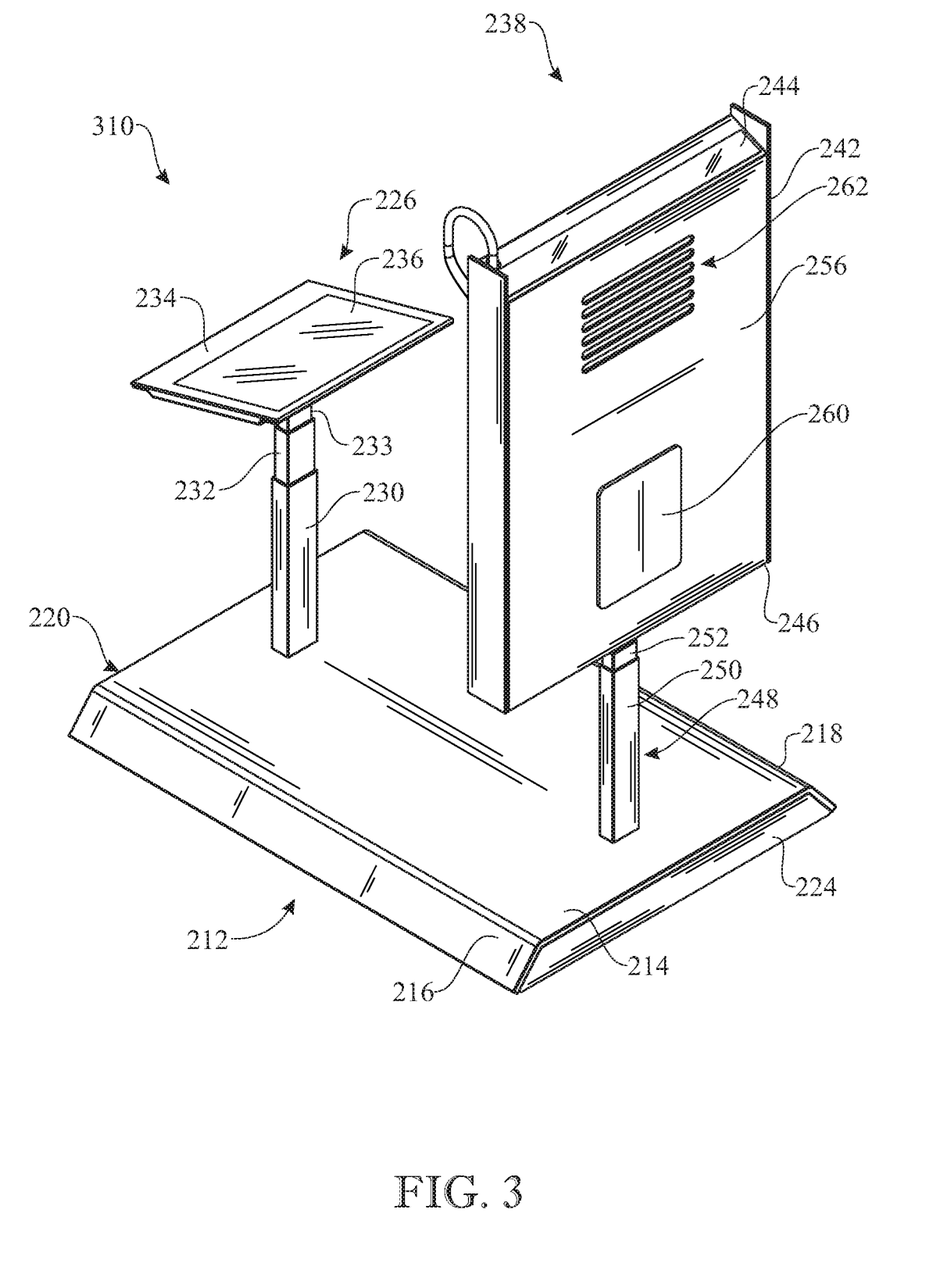
FIG. 3 presents a rear isometric view of the clinician station shown in FIG. 2.
Figure 4:
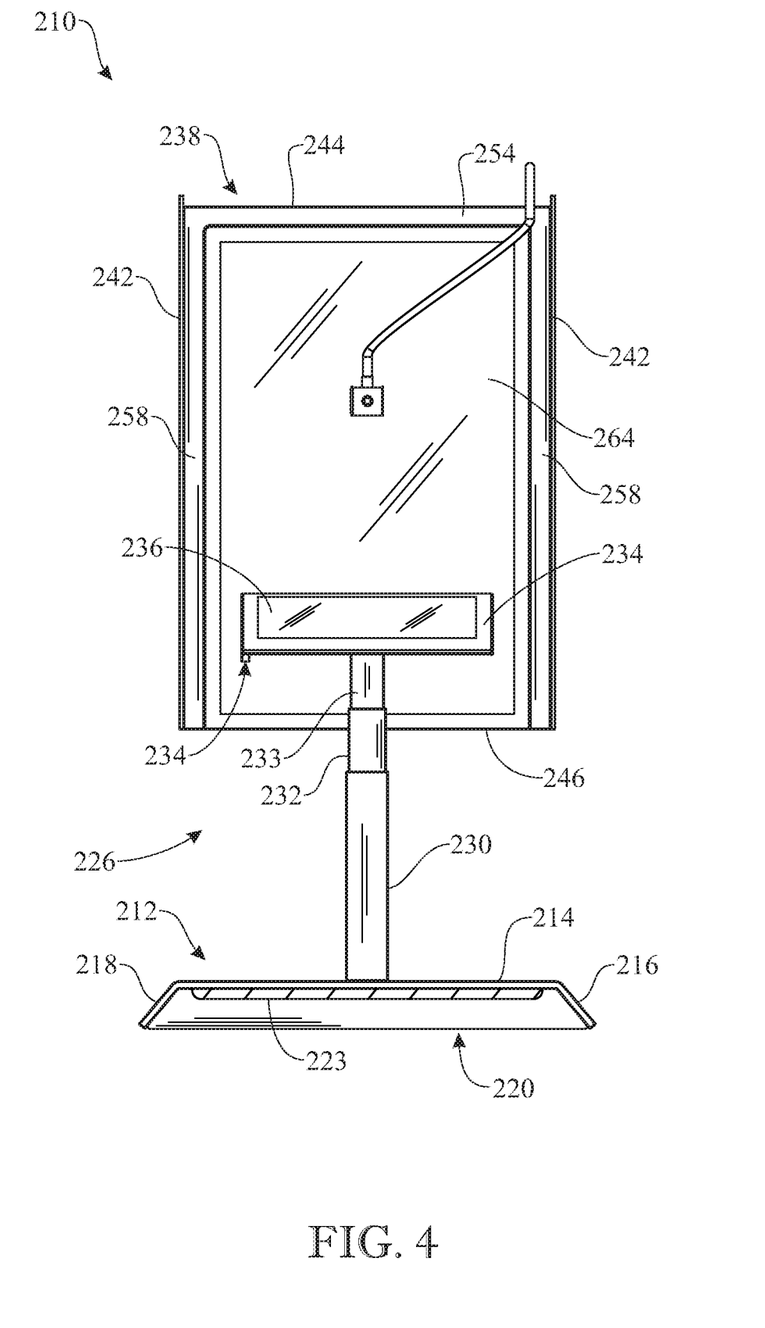
FIG. 4 presents a front side view of the clinician station shown in in FIG. 2.
Figure 5:
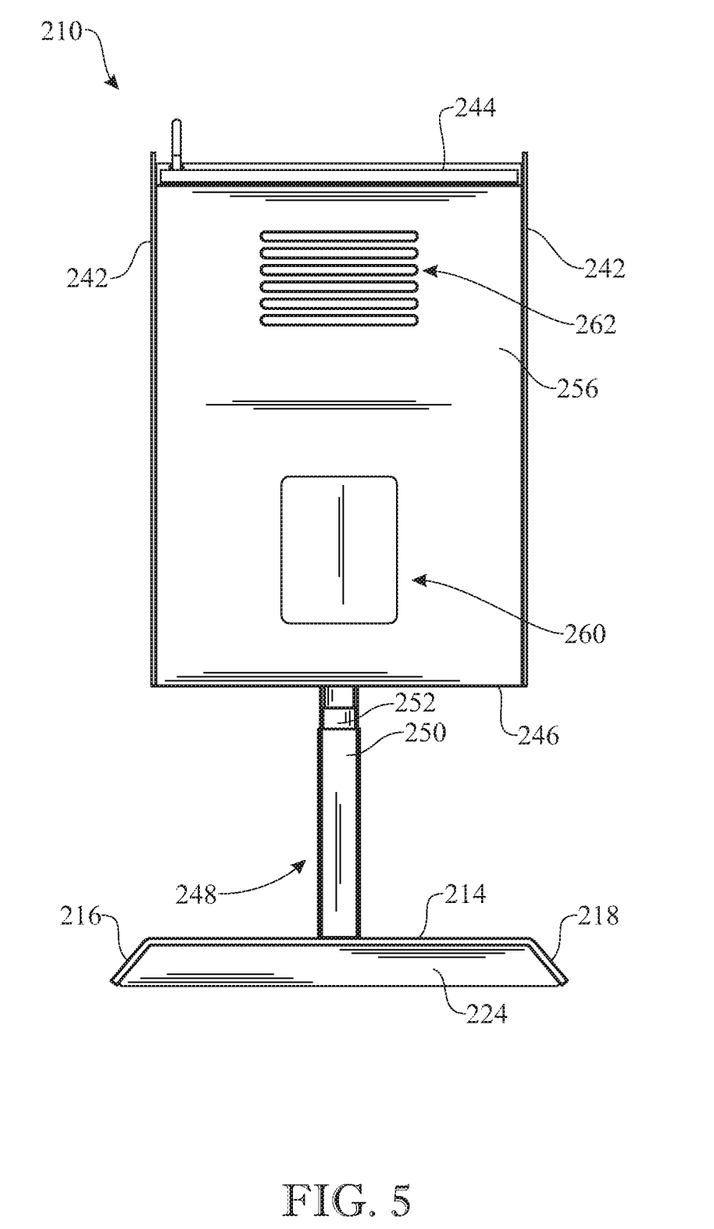
FIG. 5 presents a rear side view of the clinician station shown in in FIG. 2

Turning to FIGS. 3 and 5, the back 256 of the display terminal 238 includes a ventilation grill 262 and an access panel 260. The ventilation grill 262 helps air circulate throughout the interior spacing of the casing 240, with the access panel 260 allowing an operator or technician access to the interior spacing of the casing 240. The interior space of the casing 240 generally provides a space for all of the electrical components of the electronic display device 264 and other electrical equipment used within the clinician station 210, which may include, but are not limited to, speakers and a microphone. Similar to the base's interactive device 226, the electronic display device 264 is communicable with the network and cloud based system described heretofore. As shown in FIG. 3, the general shape of the display terminal may be provided in rectangular form. Alternative shapes for the display terminal, however, may be explored without departing from the scope of the invention, e.g., oval, circular, square, etc.

Figure 2:
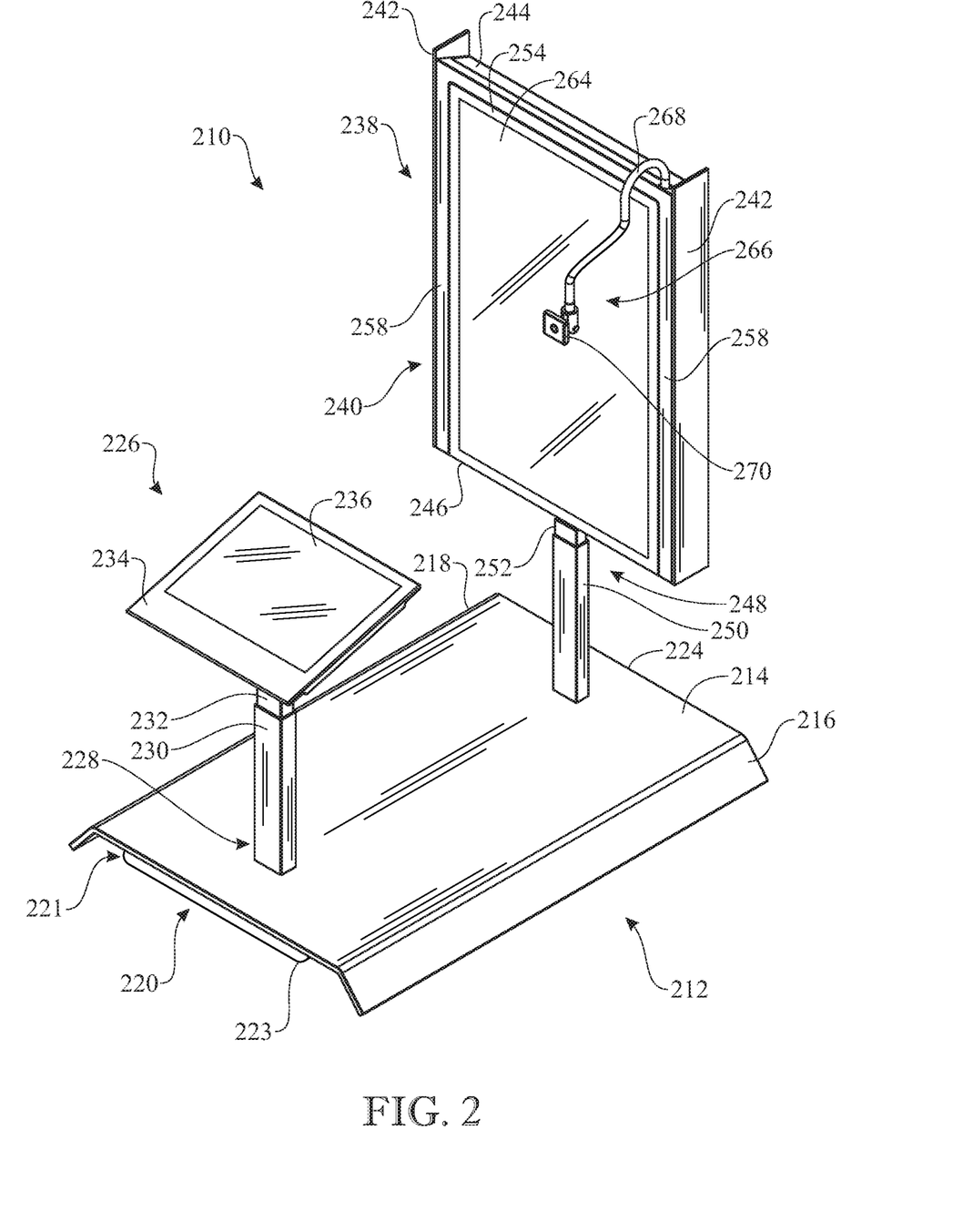
FIG. 2 presents a front perspective view of the clinician station that may be used by a clinician to communicate with a patient in a medical kiosk.
Figure 6:
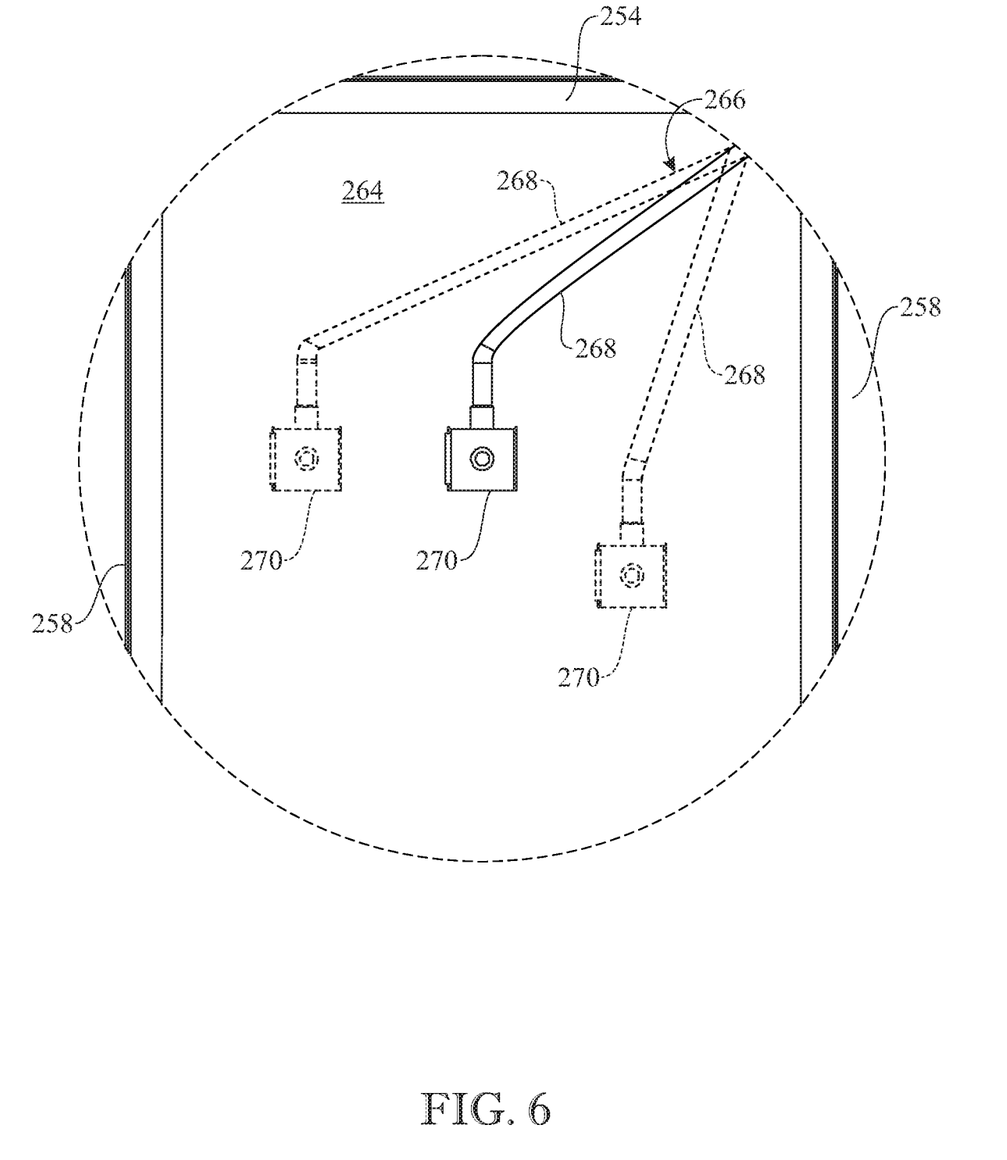
FIG. 6 presents a movable floating camera that captures and broadcasts real-time images of the user operating the clinician station.
Figure 7:
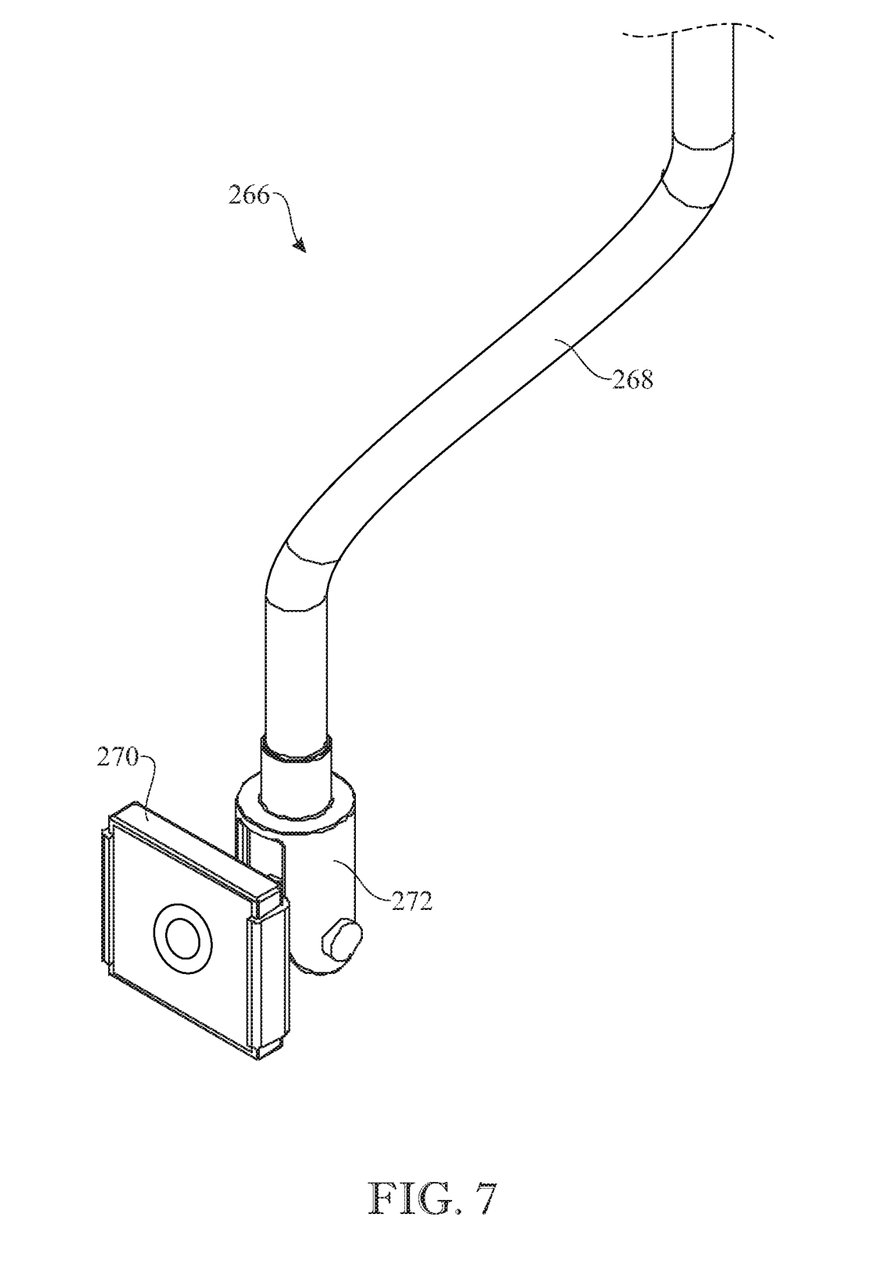
FIG. 7 presents the movable floating camera shown in FIG. 6.
Figure 8:
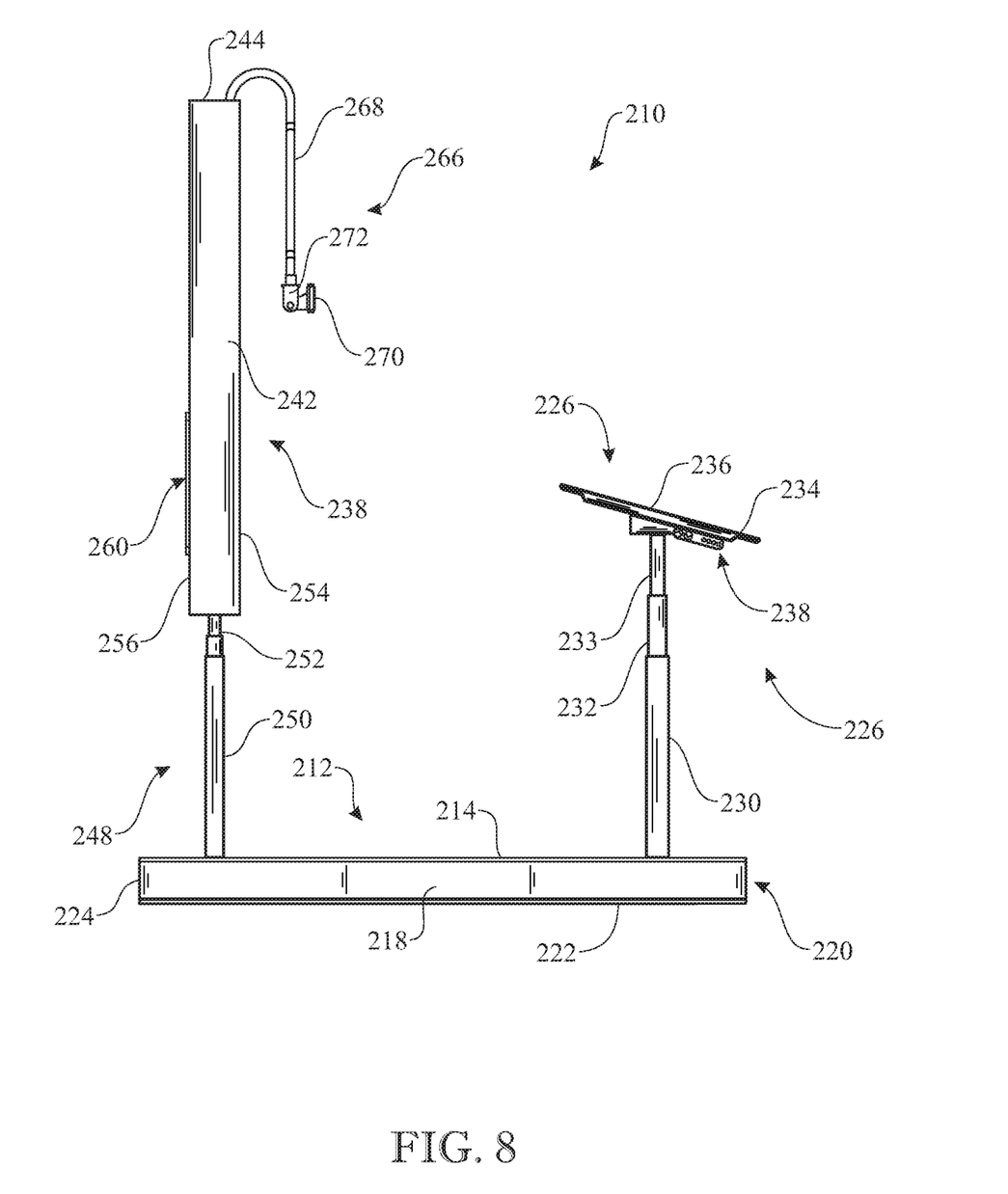
FIG. 8 presents a presents a left side view of the clinician station shown in in FIG. 2
Figure 9:
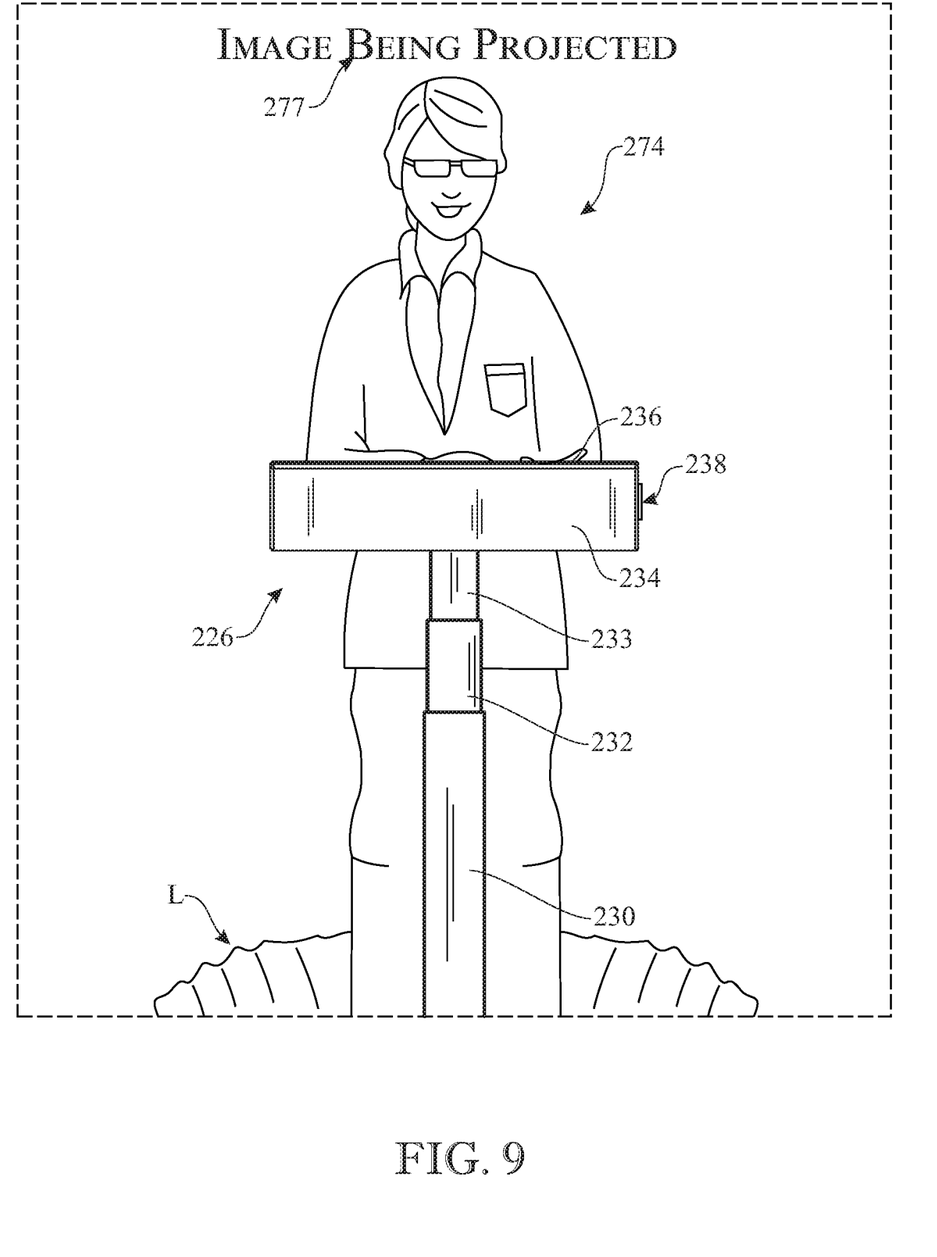
FIG. 9 presents an image of the user, operator, or clinician administering the remote medical exam being displayed inside of the medical kiosk that is occupied by a patient.
Figure 10:
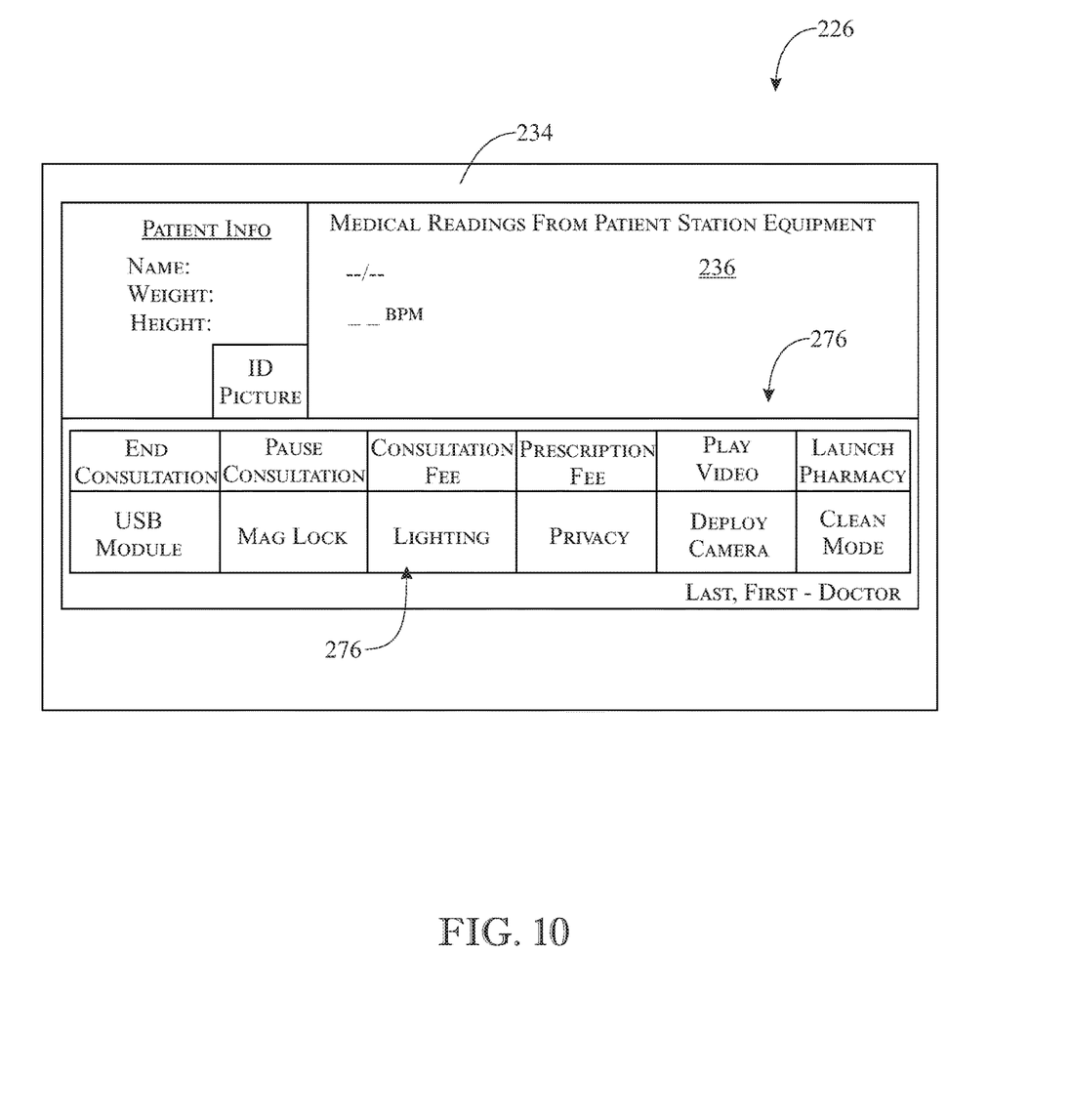
FIG. 10 presents an image of what is displayable on the user-operable interface included with the clinician station shown in FIG. 2.

Referring now to FIGS. 2 and 6-7, a floating camera 266 may be included with the clinician station 210. Although the floating camera 266 appears in the accompanying figures extending from the top 244 of the display terminal's casing 240, the floating camera 266 may be positioned elsewhere. Therefore, the position as described and illustrated in the accompanying figures should not be appreciated as limiting, but as exemplary. The floating camera 266 may comprise a goose neck or an adjustable arm 268 that may be extendable if necessary. At an end of the adjustable arm 268 sits a coupling adapter 272 that couples a camera head 270 to the adjustable arm 268. The floating camera 266 may be positioned at the eye-level of the operator operating the clinician station 210 or may be manually adjusted according to the preferences of the operator by way of the adjustable arm 268. In other words, the floating camera 266 is configured to swivel, rotate, and or produce any other necessary movements to support an optimal view of the operator using the clinician station 210. The floating camera 266 is electronically communicable with the display terminal 238, and is able to transmit a live-image of the operator to the patient in the medical kiosk (in a patient station) that is communicating with the operator (e.g., a nurse, physician, or tech) during a live remote medical session. The camera head 270 may also include a facial recognition feature that tracks the eyes of the operator, ensuring that the camera is continuously capturing a live-image of the face of the operator as he or she moves while communicating with the remote patient.

The operational use of the clinician station that may be provided in a medical facility is now discussed with reference to FIGS. 1-2 and 9-10. The description provided shall be appreciated as an example and should not be considered limiting.

In operation, an operator may enter a medical facility 202 and look for an available clinician station 210. The clinician station's terminal display 238 is communicable over the network 200 with the cloud based system 300 that hosts the medical sessions. To provide and ensure a secure, user-authorized access to a session, the operator 274 must go through an authentication process provided by the authentication server 302 of the cloud based system 300, which may include a software-based, and/or hardware-based authentication device, systems, or methods. Authentication may comprise a single-tier, two-tier, or multi-tier authentication protocol process. Examples of authentication protocols may include, but is not limited to, smart card technology, browser or digital certificates, hardware OTP tokens, software tokens, hardware security modules (HSM), or biometric authentication using one or more sensors for sensing fingerprints, hand geometry, iris or retinal patterns, or voice sampling or recognition. Other authentication protocols may include, IP security (IPSec) authentication methods, including the Kerberos protocol, private or public key certificates, or a simple pre-shared secret key, Challenge Handshake Authentication Protocol (CHAP), or the Extensible Authentication Protocol (EAP). Authentication based on single or multiple tier authentication system may include for example, use of a name/password, setting up answers to challenge questions, setting-up image recognition, or providing numerical or alphabetical information in a captcha text-entry box. The operator 274 may be go through the authentication process by utilizing the interactive electronic device 236 on the station's interactive device 226. The operator's identification process may also be done on a remote terminal device 204 (FIG. 1) configured to connect to the cloud based system and patient kiosk to oversee a medical session.

After the operator 274 has been successfully authenticated, the cloud based system 300 initiates a search query for remote medical sessions that have been initiated by remote patients in patient stations looking for a match. Once having found a match, the cloud based system establishes a connection between the clinician station 210 that is available and the patient station that is looking for a match. The process of facilitating or hosting a medical session executed by the cloud based system 300 may be carried out by a tangible computer-readable storage medium that holds machine-readable instructions executable by a logic machine (i.e. one or more processors or programmable control devices) to provide, implement, perform, and/or enact the described methods, processes and/or tasks. When such methods and processes are implemented, the state of the storage machine may be changed to hold different data. For example, the storage machine may include memory devices such as internal or external hard disk drives, CD, or DVD devices. The logic machine may execute machine-readable instructions via one or more physical information and/or logic processing devices. The logic machine may be configured to execute instructions to perform tasks for a computer program, and/or may include one or more processors to execute the machine-readable instructions. The computing system may include a display subsystem to display an application interface, or graphical user interface (GUI), or any visual element of the methods or processes described above.

Once the operator 274 on a clinician station 210 has been matched with a patient (not shown), the clinician station 210 is impregnably linked with the patient station 102 being used by the patient, giving the operator functional control over some of the electrical components provided inside the respective patient station, e.g., the station's security system, sanitation system, diagnostic camera, and other medical equipment. The establishment of a connection also enables bidirectional connection between the operator and patient using each respective station. Both the patient and operator 274 are able to virtually see one another and communicate through the speakers and microphones included in each respective station (i.e., clinician station and patient station). The floating camera 266 that is connected to the display terminal broadcasts a live image of the operator 274 speaking to the patient through the network, and a camera provided inside of the patient station broadcasts a live-image of the patient to the operator displayable on the station's electronic display 264. An exemplary image of what may potentially be broadcasted to the patient can be readily seen in FIG. 9. As shown, the patient (partaking in the remote medical session in the patient station) is able to see the color-coded light L being emitted from the light source 223 located at the base 212 of the clinician station. The light, as previously described heretofore, informs the patient of the title or status of the operator. In other words, it informs the patient that the operator is either a nurse, physician, pharmacist, a tech, a clinician, or something else. The patient may also see the face of the operator 274 standing behind the station's interactive device 226. In some instances, should it be deemed applicable, the background behind the operator 274 may include an image that is projected from a projector or the like. The image may include, but is not limited to, a logo 277, a brand, or the name of the insurance company sponsoring the remote medical session, or the name of the service provider hosting the remote medical session.

Referring now to FIGS. 1, 2 and 9-10, once a connection has been established between the clinician station 210 being operated by an operator 274 and a patient (in a patient station 102), the operator 274 may be able to provide the patient with security and privacy by engaging the patient station's security system when pressing on the interactive electronic display icon 276 (i.e., maglock and privacy icon). The maglock secures the patient station, while the privacy system activates a privacy feature on the station's glass which prevents others from peering into the patient station. Likewise, the operator 274 may control the patient station's 100 lighting system, privacy system, camera system, sanitation system, and prescription system by engaging the respective interactive icons 276 on the electronic display 236. The operator 274 is also able to see the patient's information and or measurement readings taken through the plurality of medical equipment provided in the patient station. The readings taken by the patient in the patient station are displayable on the interactive display device 236 and/or on the display terminal's display device 264 of the clinician station 210. It should be readily understood that the illustrations shown in FIG. 10 should be appreciated as exemplary, and alternative combinations of icons and additional configurations with additional features may be provided without departing from the scope of the invention.

As the session is coming to a close, the operator 274 may be able to dispense medication to the patient by pressing on the "Launch Pharmacy" icon 276 on the interactive display device 236, should the operator 274 deem medication to be necessary. By pressing on the pharmacy icon and following the steps to dispense a prescription, the patient station's medical inventory storage space activates to provide the patient with the prescribed medication. In the event the medication needed is not in-stock or stored by the inventory storage space, the operator 274 receives a notification on the interactive electronic display 236 (and/or display device 264). In that case, the operator 274 is able to put in an order remotely through the interactive electronic display 236 for the patient to pick up their prescription at a nearby pharmacy.

After the session has ended, the operator 274 deactivates the patient station's security system by pressing on the respective icon on the interactive electronic display 236 on the station's interactive device 226 to allow the patient to exit the station. As soon as the patient has vacated the patient station, the operator may activate the station's sanitation system, which includes an ultra-violet light, by pressing on the "clean mode" icon 276 on the electronic display 236. The patient station's ultra-violet sanitation system is designed to sterilize or sanitize the interior of the patient station by neutralizing or killing organic and inorganic matter within the station. After the room has been sanitized, a different patient seeking a medical remote session may enter the patient station and begin a session to communicate with an operator all over again.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A method of providing remote real time patient ailment diagnoses, the method comprising the steps of:
   (a) providing a clinician station communicable over a network, the clinician station comprising:
      (i) an electronic display terminal;
      (ii) a camera connected to the electronic display terminal, the camera comprising a camera head and an elongated adjustable arm, the elongated adjustable arm having a first end connected to the electronic display terminal and a second end connected to the camera head; and
      (iii) an interactive clinician device;
   (b) accessing the clinician station by an operator, wherein the operator when accessing the clinician station goes through an identification process to gain access to the clinician station, the identification process includes the operator verifying the operator's professional status;
   (c) providing a light source communicable with the clinician station, the light source emitting a light that corresponds with the operator's professional status;
   (d) adjusting a position of the camera by the operator so that the camera head is located in front of the clinician electronic display terminal, between the operator and the clinician electronic display terminal, at a height which is at eye level with the operator accessing the clinician station;
   (e) providing a patient station communicable over the network, the patient station including at least one display screen;
   (f) accessing the patient station by a patient;
   (g) linking the clinician station with the patient station to display a live-image of the operator on the display screen of the patient station with the camera head positioned at the eye level of the operator; and
   (h) visibly displaying on the display screen of the patient's station the light emitted from the light source communicable with the linked clinician station that corresponds with the operator's professional status.

2. The method of claim 1, wherein a cloud based system communicable over the network links the clinician station and the patient station.

3. The method of claim 1, wherein the interactive clinician device comprises a tablet.

4. The method of claim 1, wherein the clinician station further comprises elongated flat lighting disposed about one or more sides of the electronic display terminal.

5. The method of claim 4, wherein the clinician station further comprises at least one uninterruptable power supply (UPS) battery that energizes the clinician station in the event of a power loss.

6. The method of claim 1, wherein the clinician station has functional control over a plurality of systems provided inside of the patient station.

7. The method of claim 6, wherein the plurality of systems provided inside of the patient station include a locking system, a privacy system, and a sanitation system.

8. The method of claim 7, wherein the plurality of systems further includes a medication dispensing system.

9. The method of claim 1, wherein the adjustable arm of the camera comprises a goose neck.

10. A method of providing remote real time patient ailment diagnosis, the method comprising the steps of:
    (a) providing a clinician station communicable over a network, the clinician station comprising:
        (i) a display terminal comprising an electronic display and a casing that holds the electronic display;
        (ii) a camera system connected to the casing of the display terminal, the camera system comprising, a camera head and an elongated adjustable arm, the elongated adjustable arm having a first end connected to the casing of the display terminal and a second end connected to the camera head;
        (iii) an interactive clinician device;
    (b) accessing the clinician station by an operator, wherein the operator when accessing the clinician station goes through an identification process to gain access to the clinician station, the identification process includes the operator verifying the operator's professional status;
    (c) providing a light source communicable with the clinician station, the light source emitting a light that corresponds with the operator's professional status;
    (d) adjusting a position of the camera by the operator so that the camera head is located in front of the clinician electronic display, between the operator and the clinician station electronic display, at a height which is at eye level with the operator accessing the clinician station;
    (e) providing a patient station communicable over the network, the patient station including at least one display screen;
    (f) providing a cloud based system communicable over a network;
    (g) linking the clinician station with the patient station, wherein the clinician station and the patient station are linked by the cloud based system over the network; and
    (h) enabling bi-lateral communication between the clinician station and the patient station to display a live-image of the operator on the display screen of the patient station with the camera head positioned at the eye level of the operator;
    (i) visibly displaying on the display screen of the patient's station the light emitted from the light source communicable with the linked clinician station that corresponds with the operator's professional status.

11. The method of claim 10, wherein the cloud based system comprises a computing system, a registration authentication server, and a database.

12. The method of claim 10, wherein the clinician station has functional control over a plurality of systems provided inside of the patient station.

13. The method of claim 12, wherein the plurality of systems of the patient station include a locking system, and a sanitation system.

14. A method of providing remote real time patient ailment diagnoses, the method comprising the steps of:
    (a) providing a clinician station communicable over a network, the clinician station comprising:
        (i) an electronic display;
        (ii) a camera comprising a camera head and an elongated adjustable arm, the elongated adjustable arm having a first end connected to the electronic display and a second end connected to the camera head; and
        (iii) an interactive clinician device;
    (b) accessing the clinician station by an operator, wherein the operator when accessing the clinician station goes through an identification process to gain access to the clinician station, the identification process includes the operator verifying the operator's professional status;
    (c) providing a light source communicable with the clinician station, the light source emitting a light that corresponds with the operator's professional status;
    (d) positioning of the camera head by the operator so that the camera head is located in front of the clinician station screen, between the operator and the clinician station display, at a height which is at eye level with the operator accessing the clinician station;
    (e) providing a patient station communicable over the network, the patient station including at least one display screen;
    (f) accessing the patient station by a patient and requesting medical services;
    (g) providing a cloud based system communicable over the network;
    (h) activating a search query by the cloud based system for an available operator to match with the patient after the patient requests a medical session;
    (i) identifying the operator of steps b and c as the available operator;
    (j) linking the clinician station having the available operator with the patient station accessed by the patient in the patient station to establish the medical session, the medical session hosted by the cloud based system over the network;
    (k) enabling bi-lateral communication between the available operator in the clinician station accessing the network terminal therein and the patient in the patient station accessing a network terminal therein to display a live-image of the operator on the display screen of the patient station with the camera head positioned at the eye level of the operator;
    (l) visibly displaying on the display screen of the patient's station the light emitted from the light source communicable with the linked clinician station that corresponds with the operator's professional status.

15. The method of claim 14, wherein the cloud based system comprises a computing system, a registration authentication server, and a database.

16. The method of claim 14, wherein the available operator using the clinician station has functional control over a plurality of systems provided inside of the patient station.

17. The method of claim 16, wherein the plurality of systems of the patient station include a locking system, a privacy system, medical prescription system, and a sanitation system.

* * * * *